Figure 1:
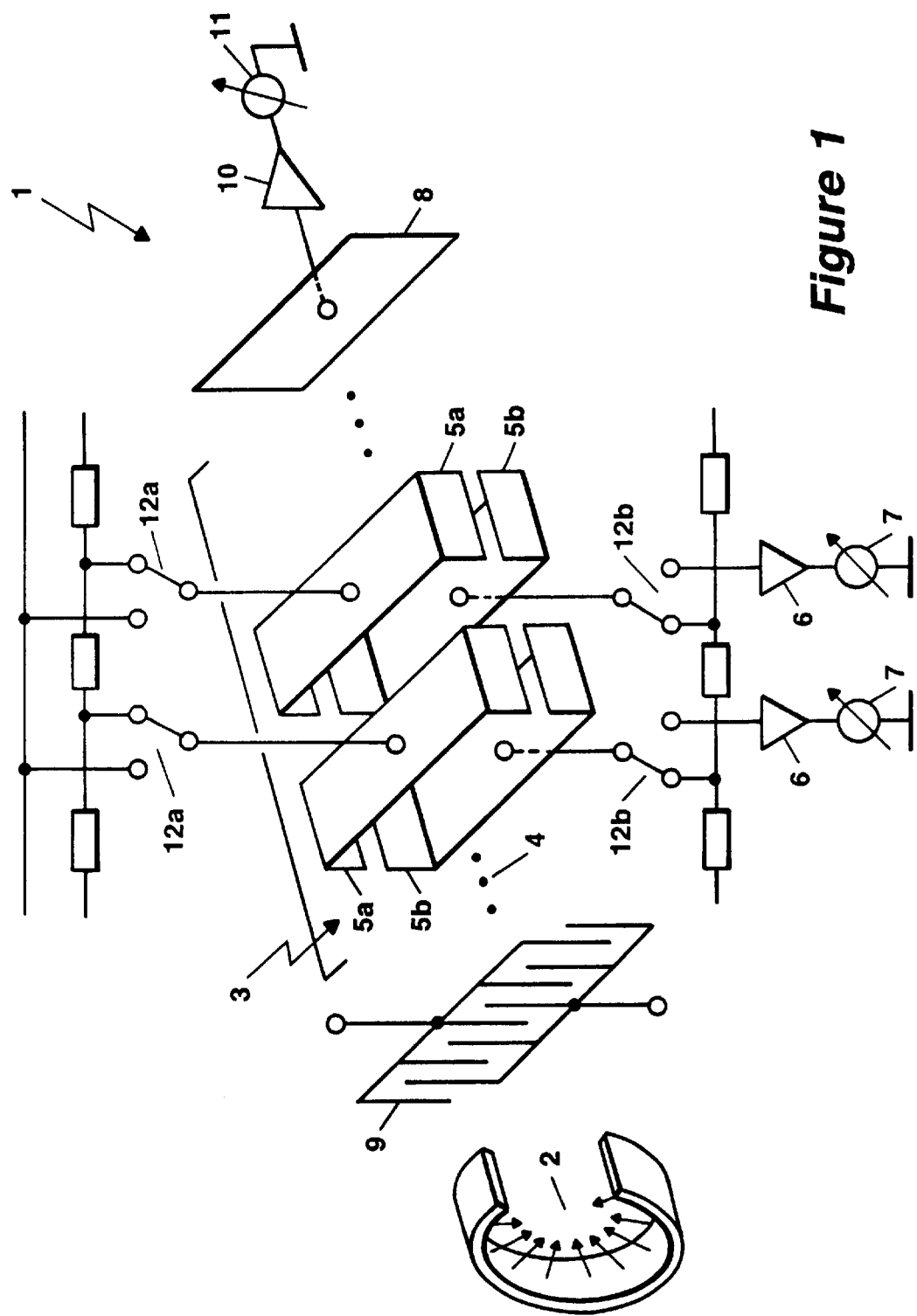

United States Patent [19]
Döring et al.

[11] Patent Number: 6,107,624
[45] Date of Patent: Aug. 22, 2000

[54] ION MOBILITY SPECTROMETER WITH SWITCHABLE ELECTRODES

[75] Inventors: Hans-Rüdiger Döring, Leipzig; Stefan Klepel, Taucha; Jörg Peuker, Leipzig; Roland Schnurpfeil, Bremen; Gerhard Weiss, Weyhe, all of Germany

[73] Assignee: Bruker-Saxonia Analytik GmbH, Leipzig, Germany

[21] Appl. No.: 09/115,341

[22] Filed: Jul. 14, 1998

[30] Foreign Application Priority Data

Jul. 18, 1997 [DE] Germany ............ 197 30 898

[51] Int. Cl.⁷ ............ H01J 49/00; B01D 59/44
[52] U.S. Cl. ............ 250/286
[58] Field of Search ............ 250/287, 282, 250/286

[56] References Cited

U.S. PATENT DOCUMENTS

| | | | |
|---|---|---|---|
| 4,855,595 | 8/1989 | Blanchard | 250/287 |
| 5,280,175 | 1/1994 | Karl | 250/287 |
| 5,420,423 | 5/1995 | Linden | 250/281 |
| 5,445,417 | 8/1995 | Bromer et al. | 281/46 |
| 5,455,417 | 10/1995 | Sacristan | 250/287 |
| 5,587,581 | 12/1996 | Stroosnyder | 250/287 |
| 5,719,392 | 2/1998 | Franzen | 250/282 |
| 5,789,745 | 8/1998 | Martin et al. | 250/286 |
| 5,905,258 | 5/1999 | Clemmer et al. | 250/287 |

FOREIGN PATENT DOCUMENTS 2198579  6/1988  United Kingdom.

OTHER PUBLICATIONS

Gary Alan Eiceman et al., *Ion Mobility Spectrometry*, CRC Press, 1993.
Timothy W. Carr, *Plasma Chromatography*, Plenum Press, 1984.

*Primary Examiner*—Seungsook Ham
*Assistant Examiner*—John Patti

[57] ABSTRACT

The invention relates to a switchable ion mobility spectrometer (IMS) with ring electrodes divided into half-rings, which surround the drift chamber of the IMS. In a first operating condition, the two half-rings of each ring electrode are at the same potential and the various ring electrodes are at different potential varying monotonously along the drift path. In this way, ions are transported in the conventional manner along the drift path. In a second operating mode, the half-rings of the ring electrodes are at different potentials, by which the ions are each deflected toward one of the half-rings. The currents thus resulting are captured by the corresponding half-rings, amplified and an ion mobility spectrum is produced. A favorable design for the IMS can be used in many different modes of operation.

11 Claims, 1 Drawing Sheet

ION MOBILITY SPECTROMETER WITH SWITCHABLE ELECTRODES

FIELD OF INVENTION

Field of the invention is an ion mobility spectrometer (IMS) with an ion source, a drift tube with an axis, and a series of field generating electrode pairs arranged along this axis, whereby these electrode pairs each generate an electrical field essentially at a right angle to the axis.

Prior Art

An ion mobility spectrometer (IMS) with field generating electrodes arranged in pairs along the axis of the drift tube is known from U.S. Pat. No. 5,455,417 and schematically represented in FIG. 5 of the patent.

In this IMS, ions continuously generated in the ion source, which move along the axis of the drift tube, are deflected at a right angle to the axis regardless of their mass and arrive at one of the electrodes. Here they each generate a current which is amplified and measured as an output signal, whereby the respective electrode is a measure for the masses of ions arriving there and the respective current intensity is a measure for the number of corresponding ions. IMSs usually operate in a different operation scheme. They normally are comprised of a usually radioactive ion source which ionizes molecules of a sample gas within an ionization compartment in the IMS. Via a periodically and briefly opened switchable grid, ion packages move into a drift compartment of the IMS, where they are transported by an axial electric field via ring electrodes arranged along a tube-shaped drift compartment. Finally, they reach a collecting electrode at the opposite end of the drift compartment, where they generate a current which is amplified and measured. Since heavier ions are less mobile than light ones, they will require a longer drift time. This means the lighter ions from the original ion package arrive first and the heaviest last After the pulsed opening of the switchable grid, the current is measured at the collecting electrode as a function of time. The current intensity at a given point in time is a measure here for the concentration of ions of a specific type. The drift time, with its associated mobility, is then a measure for the respective mass of the ions. This standard type of IMS is also schematically represented in the initially cited U.S. Pat. No. 5,455,417 in FIG. 1 as the prior art. It is a great disadvantage of this standard method that the clock pulse ratio between grid opening time and total drift time must be very small and, by experience, is only about 1%, to achieve sufficient resolution. This means that only about 1% of the ionized molecules actually contribute to the measurement signal. Total drift time is determined by the slowest possibly detectable ions, the arrival of which must be awaited at the collecting electrode before a new measurement cycle can be started.

In contrast to this design, by which the ions are detected one after another temporally at a collecting electrode, it is also possible to detect various ion types, spatially separated along a path, at different electrodes simultaneously. The IMS depicted in FIG. 5 of U.S. Pat. No. 5,455,417 does not operate in pulses but instead continuously. The ions generated in an ionization compartment are not transported by means of an axial field through the drift compartment but instead by a flow of gas molecules. There are no ring electrodes arranged along the direction of flow, but instead electrode pairs which each generate an electric field aligned at a right angle to the direction of the axis, whereby ions are pulled out of the flow of gas molecules according to their mobility to different electrodes. Temporal separation of the ions with different mobility is replaced by spatial separation. The essential advantage of this design is that ions are detected continuously, i.e. a much greater share of ionized molecules are detected since all ion types are measured simultaneously. The essential disadvantage is the extremely limited resolution due to the number of electrode pairs used. A further disadvantage is that the ions are not transported via an axial electric field through the drift chamber (generally against a light counterflow from a so-called drift gas), but instead via a flow of gas molecules that is in practice difficult to regulate and stabilize, and shows different flow speeds at different distances from the axis.

The fundamental design of the IMS and its operation are well known to the specialist and are summarized, for example, in the textbooks "Ion Mobility Spectrometry" by G. A. Eiceman and Z. Karpas (CRC Press, 1994) and "Plasma Chromatography" ed. T. W. Carr (Plenum Press, 1984). Details will not be repeated here. However, the invention described further below can naturally be used in combination with the known prior art variants of the IMS.

OBJECT OF THE INVENTION

An IMS and an operating method are required whereby the resolution and sensitivity can be adapted to a large extent to the respective analytical goal.

SHORT DESCRIPTION OF THE INVENTION

This task is solved in such a way that electrode pairs each surround the drift tube in a ring shape and are connected in such a way that, in a first field mode, the electrodes of each electrode pair are at equal electrical potential, however the various electrode pairs are at different electrode potentials which vary monotonously along the axis, whereby the ions along the axis are transported toward the collecting electrode and, in a second field mode, the two electrodes each of the electrode pairs are at different potentials.

In a first and especially favorable method for producing an ion mobility spectrum of a sample substance using an IMS according to the invention, the IMS is operated in the first field mode in the beginning, the switchable grid is opened for a brief time, whereby an ion package from the ion source reaches the drift tube, drifts along the axis towards the collecting electrode, and becomes spatially separated. The IMS is then switched over to the second field mode of operation whereby ion transport along the axis is stopped immediately and the ions are deflected at their respective axial position at a right angle to the axis. Ions of one spatial segment reach one of the electrodes where they produce an ion current pulse which is amplified and measured. In this mode, one electrode each of the electrode pairs serve as partial ion current detector electrodes. An ion mobility spectrum of the sample substance is determined here by the finite number of electrode pairs, whereby resolution is limited by the axial distance between adjacent electrode pairs.

Preferably, those electrodes of each electrode pair that the ions reach are all essentially at ground potential in the second field mode. This eases connection of the amplification and detection electronics.

In contrast to the conventional IMS method with time-resolved measurement, this method has the advantage of a reduced measuring time. It is not necessary to wait until the slowest type of ions has arrived at the collecting electrode. The entire spectrum can be measured simultanously at a time where the fastest ion type just reaches the detection electrode. Heavier ion types are distributed along the axis of the drift tube at this point in time. This can considerably reduce the measuring time. However, a degradation of resolution must be accepted for heavy ions. In many cases, this can be tolerated. If not, measurement can be repeated if necessary, whereby the spectrum is scanned at a later relative point in time. Lighter ions are usually not of interest, they have left the drift tube at this point in time. Resolution is improved for the heavier ions still present in the tube.

Also especially favorable is a method for operating an IMS, whereby the IMS, during a first partial measurement, is initially in the first field mode for detection of relatively light ions of interest, whereby the switchable grid is opened briefly, by which an ion package moves from the ion source to the drift tube, where it is transported toward the collecting electrode along the axis, whereby the light ions arrive at the collecting electrode one after the other temporally, according to their mobility, where they produce a current which is amplified by temporal resolution and measured. The IMS then is switched over to the second field mode for the detection of remaining relatively heavy ions of interest. In this way, the entire ion mobility spectrum of the sample substance of interest is obtained by two partial measurements.

SHORT DESCRIPTION OF THE PICTURE

FIG. 1: Arrangement of the essential components of an ion mobility spectrometer according to the invention.

FAVORABLE EMBODIMENTS OF THE INVENTION

Specifically, FIG. 1 shows very schematically the essential components of an ion mobility spectrometer 1 according to the invention, which is inside a gas-tight housing, not shown for the benefit of a clear view. As already mentioned initially, the standard parts and their function are no longer indicated specifically for an ion mobility spectrometer.

Proceeding from an ion source 2, ions of interest from a sample gas pass a switchable grid 9 and move into a drift tube 3. Here they are transported along an axis 4. This occurs in a first field mode through an essentially axially directed electric field. This is generated in such a way that the drift tube 3, as is typical in standard ion mobility spectrometers, is surrounded by a number, e.g. 20, of identical electrode rings (5a, 5b) which are insulated from one another generally by ceramic rings. Via a resistance network, the rings (5a, 5b) are connected in the first field mode (shown) to a high voltage source (approx. 500 V–2,500 V), so that the potential from one ring to the next constantly increases. Generally, a linear potential characteristic over the axis is sought. Usually a weak gas flow is directed in the opposite direction to ion drift along the axis 4. The electrode rings are each designed as pairs of electrodes (5a, 5b). In the first field mode shown, both electrodes (5a, 5b) of a pair are at the same potential via switches 12a and 12b. These potentials can be varied integrally or individually as required.

In a second field mode, switches 12a and 12b can be operated at the same time. Then the lower electrodes 5b (via switch 12b and the detection electronics 6, 7) in FIG. 1 are essentially at ground potential. The upper electrodes 5a are then shorted together via switch 12a at a different potential. This potential is also adjustable.

The points along axis 4 symbolize the arrangement of a whole number of identical electrode pairs (5a, 5b) along axis 4. The greater this number is, the better the resolution for detection via detection electronics 6, 7. Particularly with miniaturization by means of microfabrication techniques, the number can be greatly increased if necessary beyond the number of about 20 for a current model.

The embodiment example in FIG. 1, in addition to the electrodes 5b for detection of ions in conjunction with their respective detection electronics 6, 7, also includes another rather conventional collecting electrode 8 at the end of the drift tube 3 with its designated detection electronics 10, 11. This also allows conventional, time-resolved IMS measurements, which greatly increases the variability of the unit. It can therefore be operated in both field modes shown for example in FIG. 1 and 5 of the initially cited U.S. Pat. No. 5,455,417, and moreover in a unique, individual operating mode which, according to the application, approaches more the one or the other extreme.

In the operating method for the IMS according to FIG. 5 of the above-cited patent, the IMS is always in the second field mode whereby the switchable grid always remains open, and ions from the ion source pass into the drift tube by means of a gas stream where they are transported by the gas stream toward the collecting electrode along the axis. Due to the electric fields at a right angle to the axis, the ions are deflected to the electrodes transversely in accordance with their mobility, and reach one of the electrodes where they produce currents which are amplified and measured. In this way, a digitized ion mobility spectrum of the sample substance is determined by the finite number of electrode pairs, whereby the resolution is limited by the axial distance between adjacent electrode pairs. This method works continuously and requires no switching operations.

A further development varies the potential difference between at least one electrode pair or two axially consecutive electrode pairs between successive spectra. In this way, the measured spectrum can be locally adapted to the quite coarse axial structure of the electrode rings. Preferably the potential difference between the electrodes is changed in such a way that the digitization points of the second ion mobility spectrum fall within the scanning gaps of the first ion mobility spectrum. In this way, at least in areas of special interest in the IMS spectrum, the resolution can be increased. This modification can be applied both to the axial drift voltage (integrally or locally) as well as in the second field mode to the voltages between the electrodes of one, several or all pairs. In both cases, the axial positions of the points of impact on the detection electrodes can be shifted. Since isolation rings of finite axial expansion are attached between the electrodes, and the electrodes themselves have a finite axial expansion, displacement of about half the cycle of the arrangement is possible.

It is also preferable to change, between consecutive measurements, the potential difference between the electrodes systematically in such a way that one digitization point agrees with a maximum of one peak of the ion mobility spectrum. Due to the relatively coarse resolution of the detection electrode structure, it may happen that a partial ion cloud, corresponding to a specific ion type of interest, hits the detection electrode area just between two electrode rings. In this way, the corresponding peak is distributed over two electrodes, and a considerable amount of ions is not detected at all. It is therefore advantageous to shift the corresponding peak a little by slightly varying one of the above-mentioned voltages, so that as many ions as possible from this partial ion cloud hit one electrode precisely. This can be integrated automatically into the measurement software analogous to automatic frequency control, e.g. in the radio transmission range (so-called AFC).

Furthermore, the IMS can also always be in the first field mode, whereby the switchable grid is opened briefly, by which an ion package moves from the ion source into the drift tube, where it is transported toward the collecting electrode along the axis, so that the ions arrive at the collecting electrode, one after another temporally, according to their mobility, where they produce a current which is amplified with highest temporal resolution and measured.

Naturally the methods described above need not be used only in the respective combination mentioned but also in any other combination or alone, without leaving the scope of the invention.

What is claimed is:

1. Ion mobility spectrometer (IMS), comprising
   1) an ion source,
   2) a switchable grid,
   3) a drift tube with a central axis,
   4) a series of field supporting electrode pairs along this axis, and
   5) a series of switches and voltage generation devices whereby the electric field between the field supporting electrode pairs is switchable from a field in axial direction, defining a first field mode, to a field in a direction essentially orthogonal to the axis, defining a second field mode, and wherein one electrode of each of the electrode pairs can be connected to amplification and detection electronics to serve as a partial ion current detector electrode.

2. IMS as in claim 1, wherein a collecting electrode is mounted at the end of the drift tube.

3. IMS as in claim 1, wherein the partial ion current detector electrodes of each electrode pair are, in the second field mode, essentially at ground potential.

4. Method for producing an ion mobility spectrum of a sample substance using an IMS according to claim 1, comprising the steps of
   1) switching the IMS into the first field mode,
   2) opening briefly the switchable grid thereby allowing an ion package to move from the ion source into the drift tube,
   3) moving the ion package by the field along axis toward the collecting electrode, thereby separating ions of different mobility spatially,
   4) switching the IMS into the second field mode, thereby stopping the ion movement along the axis and moving the ions orthogonally to the axis towards the ion detector electrodes, and
   5) measuring the ion mobility spectrum as a pattern of the individual ion currents at the partial ion current detector electrodes.

5. Method for operation of an IMS according to claim 1, wherein the part of the ion mobility spectrum with ions of higher mobility is measured conventionally by the collecting electrode at the end of the drift tube, and the spectrum part with ions of lower mobility is measured according to method steps comprising:
   a) switching the IMS into the second field mode, thereby stopping the ion movement along the axis and moving the ions orthogonally to the axis towards the ion detector electrodes, and
   b) measuring the ion mobility spectrum as a pattern of the individual ion currents at the partial ion current detector electrodes.

6. Method for operation of an IMS according to claim 2, wherein the ion mobility spectrum may be measured conventionally by the collecting electrode at the end of the drift tube.

7. Method for operation of an IMS according to claim 1, wherein the IMS is always in the second field mode, the switchable grid always remains open, ions from the ion source reach the drift tube and are continuously moved by a gas stream in axial direction without mobility separation, and in transverse direction according to their mobility in the electric field, thereby arriving at the various partial ion current detection electrodes separated by their ion mobility.

8. Method according to claim 4, wherein the potential difference between at least two consecutive successive electrode pairs is varied between successive spectra measurements.

9. Method according to claim 4, wherein the potential difference between the electrodes of at least one electrode pair is varied.

10. Method according to claim 4, wherein the potential difference between the electrodes between two consecutive measurements is varied in such a way between two successive spectrum measurements that the measured ion currents from the second ion mobility spectrum cover the scanning gaps of the first ion mobility spectrum.

11. Method according to claim 4, wherein the potential differences between the electrodes between consecutive measurements are systematically changed in such a way that a peak maximum of the ion mobility spectrum coincides with the position of and is measured fully at one partial ion current detection electrode.

* * * * *